United States Patent
Rice et al.

[19]

[11] Patent Number: 5,972,188
[45] Date of Patent: *Oct. 26, 1999

[54] MEMBRANE LOADER FOR GEL ELECTROPHORESIS

[75] Inventors: Sallie Rice, Chula Vista; Charles Browning, San Diego; James Burke, San Marcos; Loi Nguyen, San Diego, all of Calif.

[73] Assignee: Genetic Biosystems, Inc., San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/675,467

[22] Filed: Jul. 3, 1996

Related U.S. Application Data

[63] Continuation-in-part of application No. 08/397,898, Mar. 3, 1995, abandoned.

[51] Int. Cl.[6] .......................... G01N 27/26; G01N 27/447
[52] U.S. Cl. .......................... 204/456; 204/466; 204/467; 204/606; 204/616; 204/618
[58] Field of Search .................................... 204/606, 613, 204/614, 616, 456, 462, 464, 466, 467; 618; 422/99, 100; 436/180

[56] References Cited

U.S. PATENT DOCUMENTS

| | | | |
|---|---|---|---|
| 4,334,879 | 6/1982 | Fujimori | 436/174 |
| 4,668,363 | 5/1987 | Gebott et al. | 436/516 |
| 4,707,235 | 11/1987 | Englert et al. | 204/461 |

(List continued on next page.)

FOREIGN PATENT DOCUMENTS

| | | |
|---|---|---|
| WO 94/11529 | 5/1994 | WIPO . |
| WO 95/30773 | 11/1995 | WIPO . |

OTHER PUBLICATIONS

Hoffman, et al., "Binding of Antibodies and Other Proteins to Nitrocellulose in Acidic, Basic, and Chaotropic Buffers", *Analytical Biochemistry*, 198:112–118 No month available (1991).

Haas, et al., "Horizontal polyacrylamide gel electrophoresis for the seperation of DNA fragments", *Electrophoresis*, 15:153–158 No date available (1994).

Technical specification for Pharmacia PhastSystem® electrophoresis system No date available.

Pharmacia Biotech Data File, *DNA Sequencing* No date available.

*Primary Examiner*—William H. Beisner
*Assistant Examiner*—John S. Starsiak, Jr.
*Attorney, Agent, or Firm*—Lyon & Lyon LLP

[57] ABSTRACT

An apparatus and method for loading samples into a gel of an electrophoretic gel system (EGS). The preferred sample loader includes a membrane having a net negative charge, net neutral charge or no charge (preferably nitrocellulose or nylon) which releasably retains the samples such that the samples are actively released when the membrane is inserted into the gel of an EGS. In one preferred embodiment, the sample loader includes a substrate having a plurality of sample loading areas extending therefrom. In an alternative embodiment, the membrane is substantially thick and serves as its own substrate. In another embodiment, sample inhibiting agents such as hydrophobic ink are formed through the membrane to inhibit the diffusion of samples between sample loading areas. Each sample loading area includes an affixed membrane. In use, one or more samples to be subjected to electrophoretic action are applied to the membrane before the membrane is inserted into a previously polymerized gel. The membrane advantageously prevents contamination of electrode buffer solution and cross-talk or mixing between samples by inhibiting the diffusion of sample material into the gel or buffer solution before the gel is activated by a release mechanism. Once the gel is activated by the release mechanism, the membrane releases substantially all of the samples into the gel where the samples are subjected to the electrophoretic separation and identification process.

8 Claims, 7 Drawing Sheets

U.S. PATENT DOCUMENTS

| | | | |
|---|---|---|---|
| 4,726,889 | 2/1988 | Love et al. | 204/614 X |
| 4,874,491 | 10/1989 | Stalberg | 204/466 |
| 4,883,577 | 11/1989 | Sugimoto et al. | 204/619 |
| 4,889,606 | 12/1989 | Dyson et al. | 204/614 X |
| 4,909,918 | 3/1990 | Bambeck et al. | 204/619 |
| 4,915,811 | 4/1990 | Yamamoto et al. | 204/619 |
| 5,073,246 | 12/1991 | Chu et al. | 204/619 |
| 5,217,591 | 6/1993 | Gombocz et al. | 204/466 |
| 5,275,710 | 1/1994 | Gombocz et al. | 204/461 |
| 5,284,565 | 2/1994 | Chu et al. | 204/619 |
| 5,304,292 | 4/1994 | Jacobs et al. | 204/619 |
| 5,318,682 | 6/1994 | Singer | 204/466 |
| 5,324,412 | 6/1994 | Kolner | 204/619 |
| 5,405,516 | 4/1995 | Bellon | 204/466 |
| 5,618,701 | 4/1997 | Landegren | 435/91.1 |
| 5,759,784 | 6/1998 | Asp et al. | 435/6 |

MEMBRANE LOADER FOR GEL ELECTROPHORESIS

RELATED PATENT APPLICATIONS

This is a continuation-in-part of U.S. patent application Ser. No. 08/397,898, filed Mar. 3, 1995, now abandoned.

BACKGROUND OF THE INVENTION

1. Field of the Invention

This invention relates generally to the field of gel electrophoresis, and more particularly to an apparatus and method for loading samples into a gel of an electrophoretic gel system.

2. Description of Related Art

Electrophoresis gels are widely used in biotechnology for analyzing biomolecular sample materials such as proteins and nucleic acids. In molecular biology research laboratories, it is well known to use gel electrophoresis to separate and identify sample material based on size, charge and other aspects of the sample material. Biomolecules such as DNA, RNA and protein are commonly separated using this procedure. Electrophoresis involves the migration of electrically charged particles in a gel solution or suspension in the presence of an applied electric field. Samples are inserted or loaded into the gel of an electrophoretic gel system (EGS) and thereafter an electric field is applied to the gel. Each particle in the sample moves toward the electrode having an electrical polarity which is opposite the electrical polarity of the particle. The electrophoretic mobility of a sample particle is inversely proportional to the size of the particle. Various species of a sample may be separated and identified due to differences in electrophoretic mobilities in the gel. The gel also reduces the mixing, or "cross-talk", of various sample particles during the electrophoretic process. Gel electrophoresis thereby facilitates the stable separation and identification of sample material.

Typically, the initial step in manufacturing an EGS is "casting", or polymerization, of the gel. Common techniques used to cast the gel employ a well-forming instrument such as a comb having teeth which extend downwardly toward a sample loading end of the EGS gel. In these systems, the comb teeth are inserted into the EGS gel before polymerization. After the gel polymerizes, the comb is removed from the gel, thereby forming sample wells in the gel where the teeth were inserted. One example of such a sample well-forming instrument is described in U.S. Pat. No. 5,284,565 to Chu, et al. The Chu comb forms sample wells in the EGS gel which taper downwardly toward the gel enclosure. Disadvantageously, it has proven difficult to form structurally consistent sample wells using these well-forming techniques.

Figure 1A:
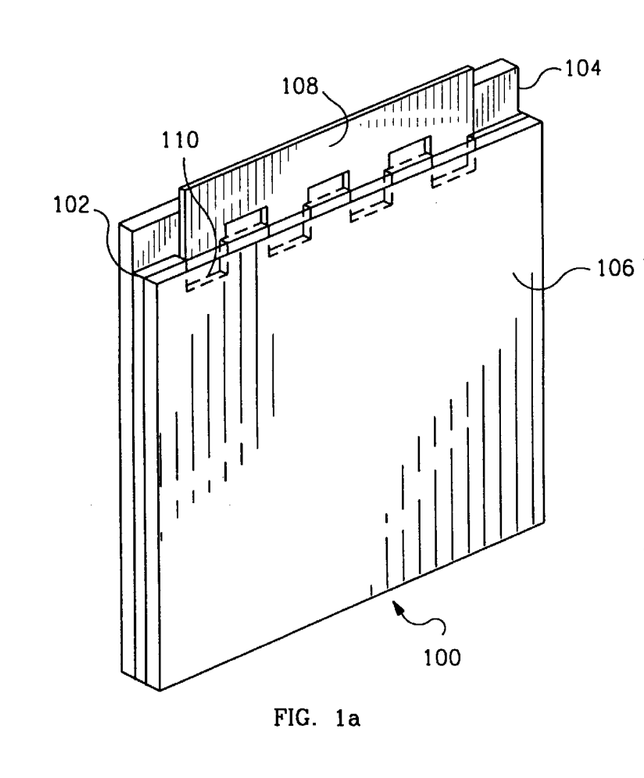
FIGS. 1a and 1b are side perspective views of an electrophoresis apparatus used in the prior art electrophoretic gel systems (EGS).
Figure 1B:
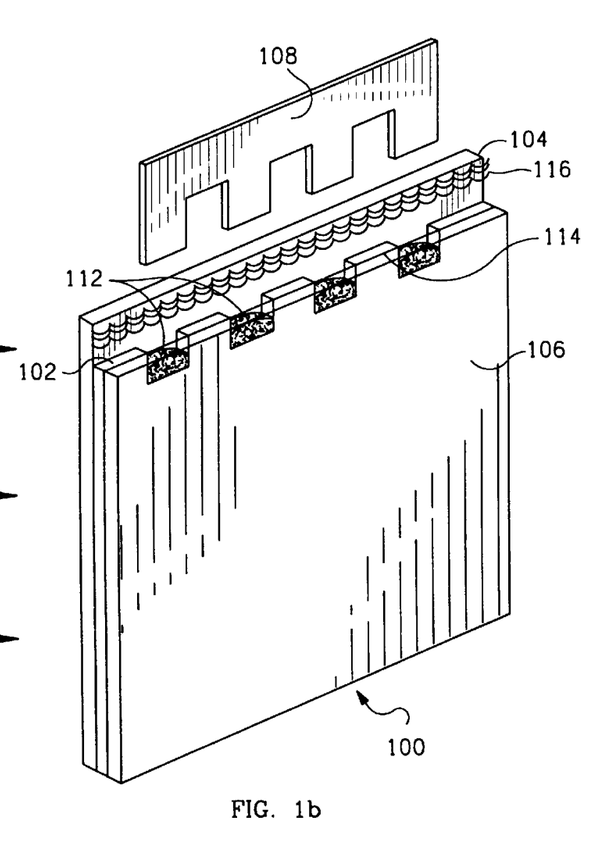

FIGS. 1–2 show a prior art electrophoretic gel system. As shown in the electrophoresis apparatus 100 of FIG. 1a, a gel 102 is disposed between two substantially rigid plates 104, 106 which are used to secure the gel 102 in place and to facilitate casting of the gel 102. The gel 102 typically comprises agarose or polyacrylamide. A well-forming comb 108 having a plurality of teeth or fingers 110 is used to form sample wells in the gel 102. As shown in FIG. 1a, the comb 108 is inserted between the plates 104, 106 into an upper edge of the gel 102 before the gel polymerizes. As shown in FIG. 1b, after the gel polymerizes, the comb 108 is removed from the upper edge of the gel 102. A plurality of sample wells 112 are thus formed between the plates 104, 106 in the upper edge of the gel 102. Liquid samples are then introduced into the sample wells 112 wherein they form individual sample pools, each separated by partitions 114 formed in the upper edge of the gel 102. To facilitate the electrophoresis process, the apparatus 100 is immersed in an electrode buffer solution. The buffer solution may be liquid, gel or paste. As shown in FIG. 1b, the apparatus 100 is immersed in the electrode buffer solution so that the level of the solution 116 is slightly below the top edge of the plate 104. After the liquid samples are introduced into the sample wells 112, an electric field is applied to the electrode buffer solution so that electric current passes through the buffer solution, sample material, and gel 102. The samples in the sample wells 112 then migrate toward the bottom of the gel and separate due to their differing migration characteristics.

Figure 2A:
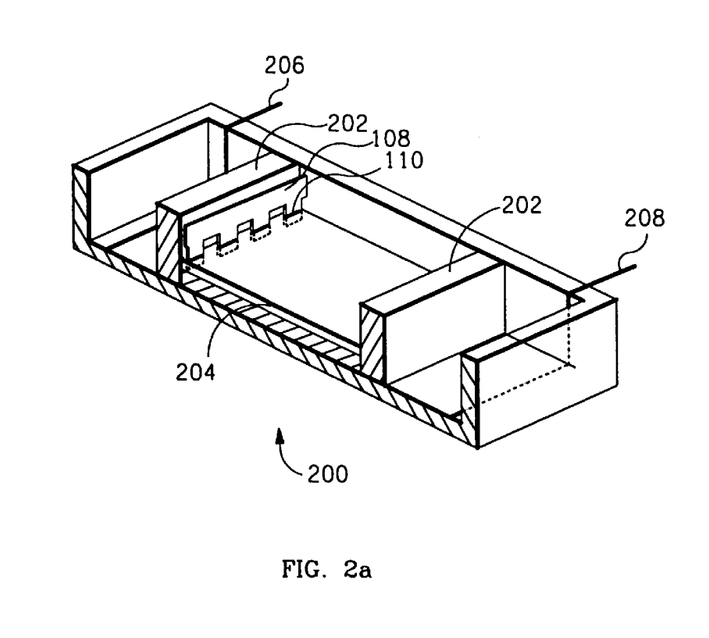
FIGS. 2a and 2b are side perspective views of the electrophoresis apparatus of FIG. 1 used in a prior art horizontal EGS.
Figure 2B:
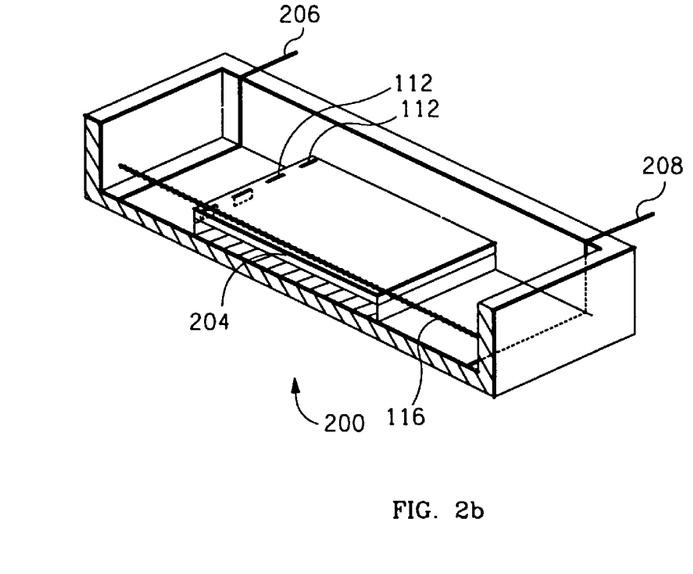

FIGS. 2a and 2b show a prior art horizontal EGS. The horizontal EGS 200 includes a gel casting structure which has two substantially rigid removable dams 202 shaped to be received by the EGS 200. Before solidification or congelation of a gel 204, the gel 204 is poured into the EGS 200 and is cast by the EGS walls and the removal dams 202. The comb fingers 110 (FIGS. 1a and 1b) are then inserted into the gel solution 204 before the gel congeals. After the gel congeals, the fingers 110 of the comb 108 are removed from the gel 204, as shown in FIG. 2b. The comb 108, and specifically the teeth 110, form sample wells 112 in the gel 204. Sample material is then typically manually inserted into the wells 112 using a pipette. One of the drawbacks of this sample insertion technique is that it requires a high degree of technical skill and dexterity. Consequently, the insertion of sample material into the wells is a time-intensive process which is prone to error and inadvertent spillage of sample material into the buffer solution. Therefore, there is a need for an improved gel electrophoresis method and apparatus which facilitates the loading of samples into an EGS.

As shown in FIG. 2b, the gel is immersed in an electrode buffer solution for electrophoretic separation. Similar to the apparatus of FIG. 1, the electrode buffer solution is filled to a level 116 which is sufficient to immerse the gel 204. The EGS 200 typically includes connections to a power supply (not shown). As shown in FIG. 2b, a cathode wire 206 is immersed in the electrode buffer solution at an upper end of the EGS 200 proximate the sample well end of the gel 204. An anode wire 208 is immersed in the buffer solution at a bottom end of the EGS 200 near a distal end of the gel 204. Thereafter, as described above, an electric field is typically applied to the buffer solution and the samples previously inserted into the sample wells 112 separate due to the electrophoretic effect.

Another prior art gel electrophoresis system and sample loader is disclosed in U.S. Pat. No. 5,275,710 issued to Gombocz et al. Gombocz teaches a sample loader or applicator which has a plurality of applicator channels covered by an absorbent material (such as a wick) which prevents the uninhibited flow of sample material into the gel. When the wicks are loaded with a measured amount of sample material, the applicator is lowered into the gel so that the wicks contact the gel, which allows the sample material to perfuse through the wicking material and into the gel. Disadvantageously, the applicator taught by Gombocz allows sample material to diffuse into the gel and surrounding buffer before the gel is activated by applying an electric field. Therefore, a need exists for a sample loading apparatus and method for loading samples into an EGS which allows samples to be easily, quickly and accurately loaded into the gel yet which inhibits the electrophoretic separation of the samples until activation by the release mechanism.

One of the problems associated with the prior art sample loading apparatuses is the potential for inadvertent cross-contamination via the buffer solution. As shown in FIG. 1b, if the samples overflow the sample wells 112, the buffer solution becomes contaminated with sample material, which may lead to erroneous results due to mixing of sample material between sample wells. Therefore, there is a need for a method and apparatus for loading sample material into an EGS which inhibits the diffusion of sample material into the gel or buffer before electrophoretic action commences.

Another drawback associated with the prior art EGS sample loading devices is due to the incomplete polymerization of certain types of gel material such as polyacrylamide due to the presence of a polymerization inhibitor. For example, due to the presence of oxygen, the area surrounding the comb teeth in prior art EGS loaders is often incompletely polymerized. Also, because the sample wells 112 are typically spaced in very close proximity to each other, the walls or partitions 114 are often quite fragile and as a result are easily damaged or destroyed. Another drawback associated with the prior art methods and apparatuses for loading samples into an EGS is the difficulty in removing undesirable materials such as urea from the sample wells after use.

Therefore, there is a need for an improved apparatus and method for loading sample material into a gel of an EGS. The present invention provides such an apparatus and method.

SUMMARY OF THE INVENTION

The present invention is an apparatus and method for loading samples into a gel of an electrophoretic gel system (EGS). The preferred sample loader includes a membrane which releasably retains the samples such that the samples are controllably released when the membrane is inserted into the gel of an EGS. In one preferred embodiment, the sample loader includes a substrate having a membrane configured as a plurality of sample loading areas. The sample loading areas are preferably diffusion-isolated from each other. Any practical means to isolate the diffusion of samples between the loading areas may be used. For example, the loading areas may be physically separated to prevent the diffusion of samples from one loading area to another. Alternatively, sample inhibiting agents such as hydrophobic ink may be applied to the membrane to inhibit the diffusion of samples between the sample loading areas.

The substrate preferably comprises a strip-like material which is non-porous, non-conductive, relatively inert, neutrally charged, and inexpensive. For example, the substrate preferably comprises either celluloid or plastic. The membrane preferably comprises either nylon or nitrocellulose. In an alternative embodiment, the membrane is substantially thick and serves as its own substrate. Depending upon the samples to be loaded, the membrane may alternatively be neutrally, negatively or positively charged.

The sample loading areas preferably correspond to multiple columns of the EGS. In use, one or more samples to be subjected to electrophoretic action are applied to the sample loading areas of the membrane before the membrane is placed in contact with a previously polymerized gel. Cross-contamination of the samples is, in part, prevented by the physical spacing between each sample loading area. The substrate is then positioned with respect to the EGS such that the sample loading areas are placed into contact with the polymerized gel immersed in buffer solution. The membrane releasably binds the samples to the sample loading areas during insertion of the sample loading areas into the gel.

The membrane advantageously prevents contamination of electrode buffer solution and cross-talk or mixing between samples by inhibiting the diffusion of sample material into the gel or buffer solution before the membrane is activated by a release mechanism. Once the gel is activated by the release mechanism, the membrane releases substantially all of the samples into the gel where the samples are subjected to the electrophoretic separation and identification process.

The membrane of the present sample loader works with several different release mechanisms. For example, the membrane will release samples when the gel is activated via the application of an electric field to the buffer solution. Also, adding salt to change the salt concentration, adding acid or base to change the pH, heating or cooling, and strengthening or weakening the buffer solution, are techniques that can be used to alter the releasing effect. Other release mechanisms include the exposure of buffer solution to radiation, light, sonic waves, electromagnetic radiation, particle bombardment, and any other means that substantially causes the release of sample material from the membrane.

The present sample loader may alternatively be used alone or in conjunction with prior art EGS gels, loading apparatuses, and loading techniques. For example, the prior art well-forming combs may first be used to form sample wells in the prior art gels for electrophoresis. Thereafter, samples may be loaded into the gels by applying the samples to the membranes of the present sample loader, and inserting the sample loader into the sample wells. Alternatively, the present sample loader may be used to form sample wells in the gel, and thereafter may be used to actively load samples in the wells by activating the gel with a release mechanism.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

Like reference numbers and designations in the various drawings refer to like elements.

DETAILED DESCRIPTION OF THE INVENTION

Throughout this description, the preferred embodiment and examples shown should be considered as exemplars, rather than as limitations on the present invention.

Figure 3A:
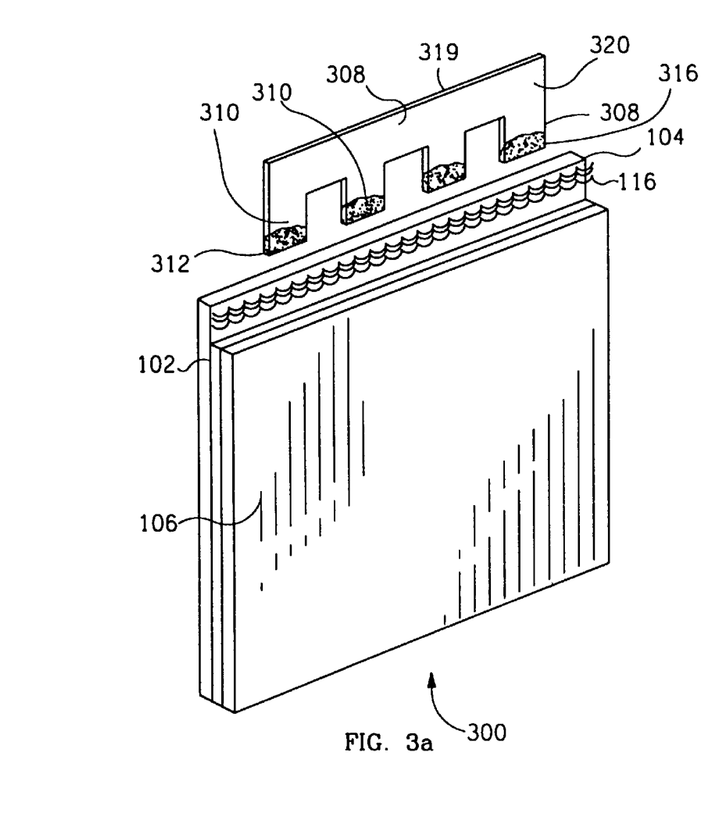
FIGS. 3a and 3b are side perspective views of one preferred embodiment of the sample loader of the present invention intended for use in a vertical EGS.
Figure 3B:
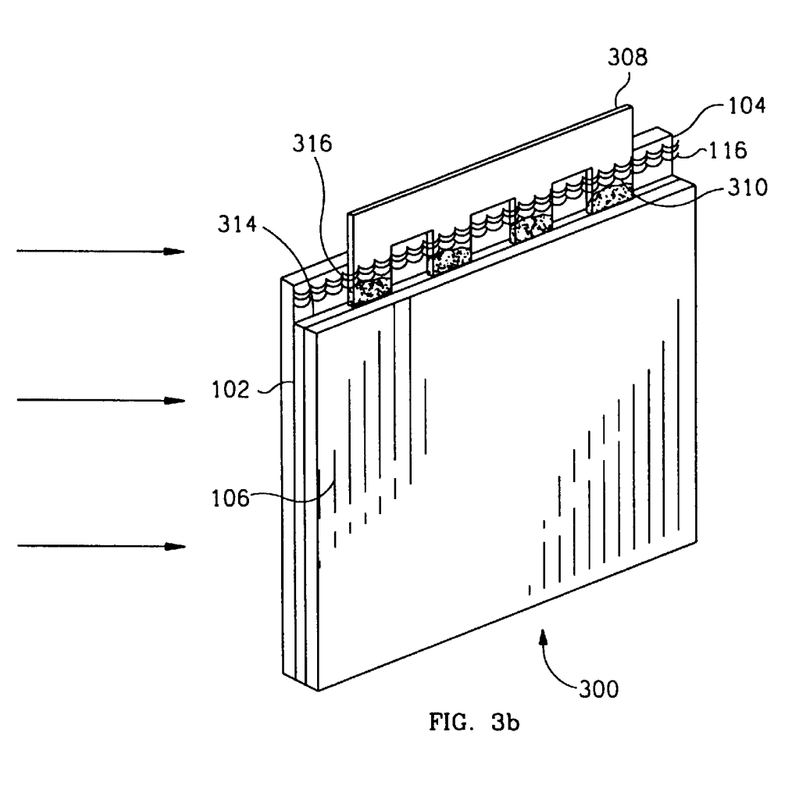
Figure 4:
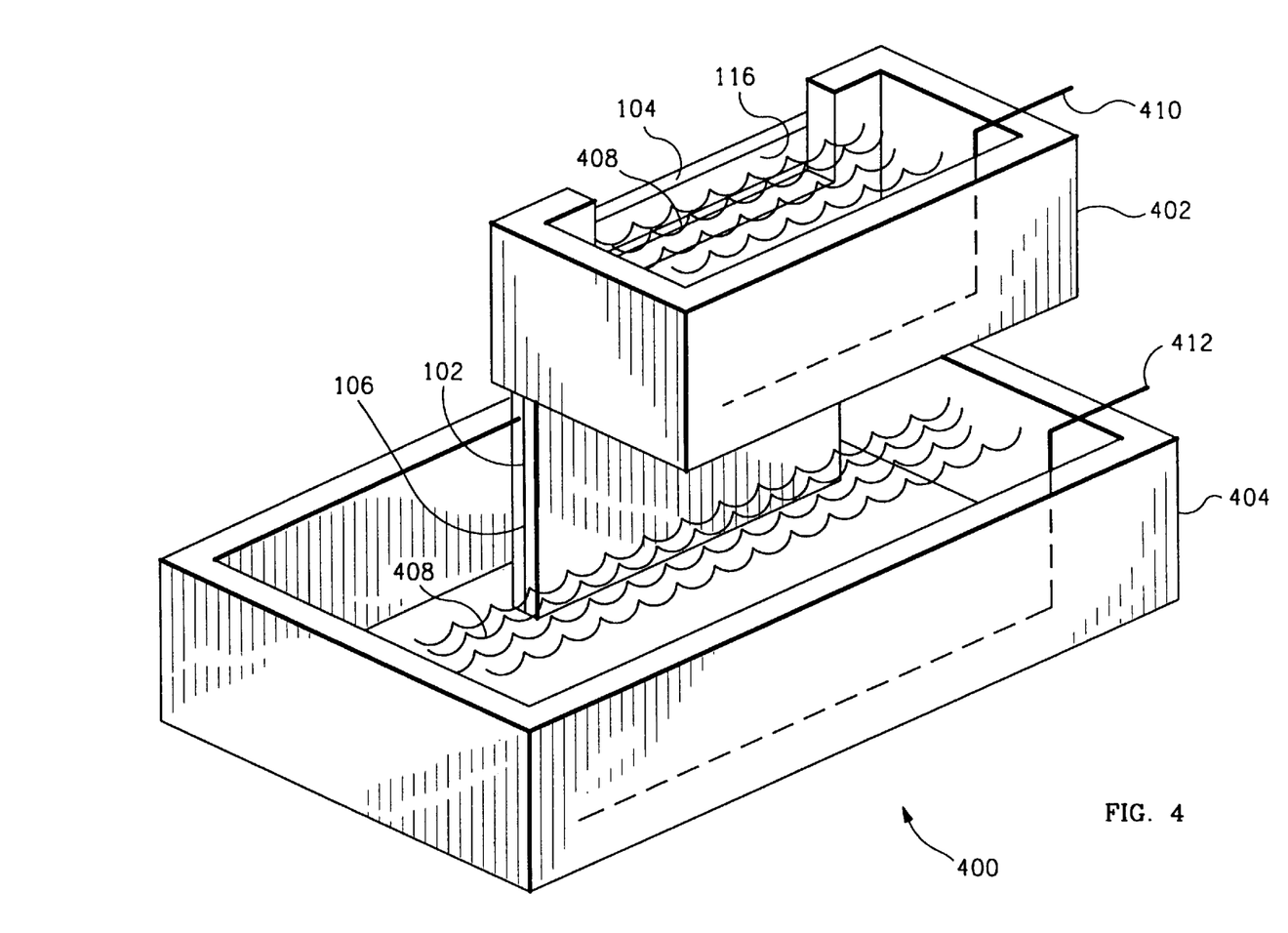
FIG. 4 is a side perspective view of a vertical EGS intended for use with the inventive sample loader of FIGS. 3a and 3b.
Figure 5A:
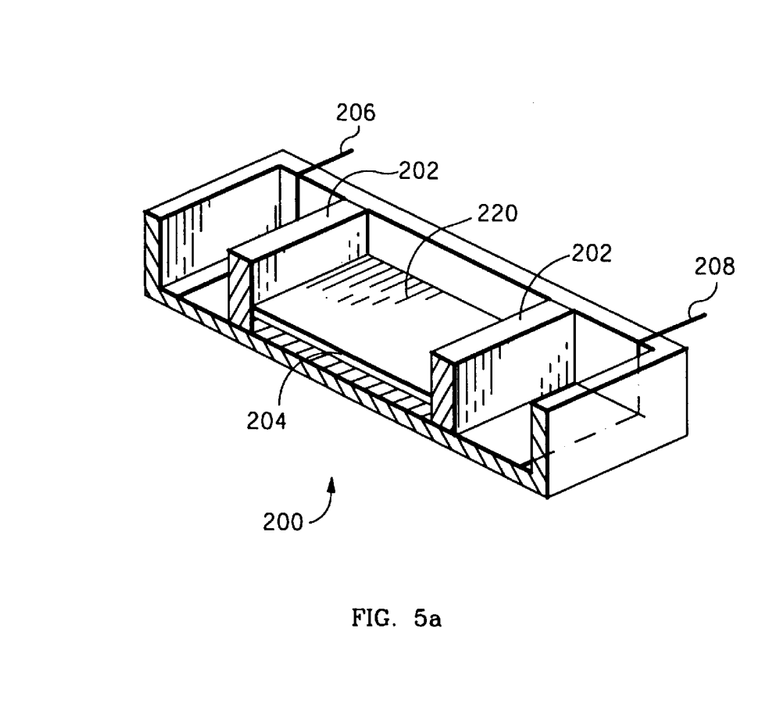
FIGS. 5a and 5b are side perspective views of prior art horizontal EGS system using the sample loader of FIGS. 3a and 3b.
Figure 5B:
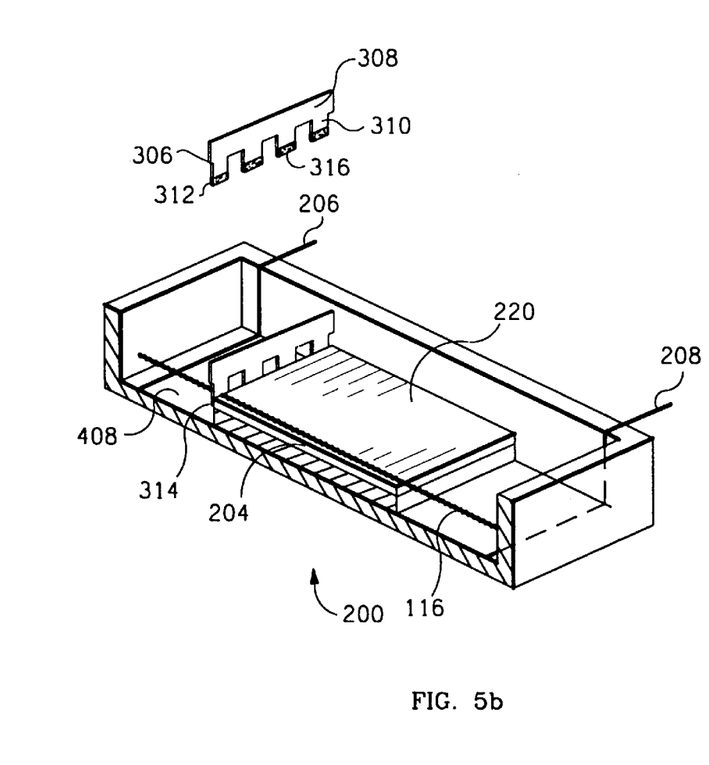

FIGS. 3–4 show one preferred embodiment of the sample loader of the present invention intended for use in a vertical EGS. FIGS. 5a and 5b show the sample loader of FIGS. 3–4 intended for use in a horizontal EGS. Referring now to FIG. 3a, the preferred sample loader 308 is shown before being placed in contact with an electrophoretic gel 102 which is disposed between two substantially rigid plates 104, 106 as described above with reference to FIGS. 1 and 2. As described below in more detail with reference to FIG. 6a, the sample loader 308, in one preferred embodiment, comprises a substrate 320 which has a plurality of sample loading fingers 310 formed in one side of the substrate 320. The fingers 310 extend downwardly away from a top edge 319 of the substrate 320. The fingers 310 preferably include a loading area 312. The loading areas correspond to the multiple columns of the EGS 200. Each loading area 312 has an affixed membrane 306. In use, one or more samples to be subjected to electrophoretic action are placed on the individual membranes 306. As described below in more detail with reference to FIG. 6a, the sample loading areas 312 are "diffusion-isolated." That is, cross-contamination of samples applied to each sample loading area is prevented in part by the physical spacing of the membranes 306 and fingers 310 or by some other convenient diffusion-isolation means.

The loader membrane 306 can have varying thicknesses and can thereby releasably retain more or less sample material. In an alternative embodiment, if the membrane 306 is sufficiently thick, it can serve as its own substrate.

The membranes 306 releasably retain or reversibly bind sample material to the loader 308. That is, the membranes 306 bind the sample material to the loader 308 when the sample is loaded or applied to the membranes 306 but actively release the sample material into the gel 102 upon activation of a release mechanism. Various types of membrane material are described below in more detail with reference to FIG. 6a.

Biomolecular samples 316 are quickly and easily applied by a technician to the loading areas 312 of the fingers 310. The fingers 310 of the loader 308 are placed in contact with a proximal upper edge 314 of the gel 102 as shown in FIG. 3b. The fingers 310 are inserted far enough into the gel 102 so that the sample material 316 on the loading areas 312 does not contaminate the buffer solution after activation of the release mechanism. That is, the fingers 310 must be inserted far enough into the gel 102 so that the sample material 316 is inserted below the buffer solution level 116 and the edge 316 so that the sample material 316 does not diffuse into the buffer solution when released from the membranes 306. Similar to the prior art EGSs described above, the buffer solution may be liquid, gel, or paste.

After the sample is loaded into the gel 102, but before activation of the release mechanism, the sample material 316 remains releasably bound to the membranes 306 of the loader 308. The membranes 306 comprise materials which diffusion-isolate applied samples until the membranes 306 are activated by a release mechanism. That is, the membranes 306 preferably allow little or no diffusion of sample material 316 into the buffer solution or gel 102 until the gel 102, and the membranes 306, are activated by a release mechanism. However, upon the application of a releasing agent, the samples elute out of the membranes 306 and into the gel 102, where they are subjected to electrophoretic separation. In the preferred embodiment, the membrane 306 is selected to releasably bind a particular sample until the EGS electric field is applied to the buffer solution. Different membrane material may be used to diffusion-isolate different applied sample types, as discussed further below.

Many different release mechanisms may be used in an EGS other than the application of an electric field to a buffer solution. For example, adding salt to change the salt concentration, adding acid or base to change the pH, heating or cooling the samples or the membrane, and/or strengthening or weakening the buffer solution can be used to alter the releasing effect. The present sample loader can be used in an EGS which uses any of these releasing agents.

FIG. 4 shows a vertical EGS 400 intended for use with the inventive sample loader 308 of FIGS. 3a and 3b. The EGS 400 includes an upper cathode tank 402 and a lower anode tank 404. After the gel 102 polymerizes between the plates 104, 106, the plates 104, 106 are inserted vertically into the anode tank 404. Electrode buffer solution 408 is poured into the lower anode tank 404 and the upper cathode tank 402. A distal bottom edge of the polymerized gel 102 is thereby exposed to the electrode buffer solution 408 in the lower anode tank 404. The upper edge 314 of the gel 102 is exposed to the electrode buffer solution 408 contained by the upper cathode tank 402 and the plate 104. As described above with reference to FIGS. 1b, 2b, and 3b, the electrode buffer solution 408 is filled in the upper cathode tank 402 to a level 116 which is below the top edge of the plate 104 yet which is sufficient to submerge the top edge 316 of the gel 102.

An cathode wire 410 is immersed in the buffer solution 408 and is preferably connected to a negative terminal of a DC power supply (not shown). An anode wire 412 is similarly immersed into the electrode buffer solution 408 within the lower anode tank 404 and connected to the positive terminal of a DC power supply.

After inserting the sample material using the sample loader 308 (FIGS. 3a and 3b) into the gel 102 as described above, samples are released out of the membrane and the electrophoretic separation process is triggered by activating the DC power supply and thereby applying an electric field to the gel 102. Advantageously, the membranes 306 diffusion-isolate the sample material 316 and the sample material 316 thereby remains essentially bound to the membranes 306 unless and until the gel 102 is activated. This diffusion-isolation or releasable retention of sample material to the membranes 306 reduces the potential for cross-talk between the different samples applied to the different fingers 310 and loading areas 312 of the loader 308. Furthermore, contamination of the electrode buffer solution 408 is prevented using the present loader 308. After the sample material 316 is applied to the loading area 312 of the fingers 310, the membranes 306 bind the sample material to the loader 308 and thereby prevent the inadvertent elution of sample material into the electrode buffer solution 408 when the sample material 316 is placed in contact with the gel 102.

The present sample loader 308 of FIGS. 3a and 3b and used in the vertical EGS 400 of FIG. 4 facilitates the efficient, accurate, inexpensive, and rapid insertion of sample material into a gel for gel electrophoresis. In contrast to the prior art sample loaders described above, little technical skill or dexterity is required to load samples into an EGS using the present sample loader. Samples can be quickly applied to the fingers 310 and more specifically the membranes 306 of the loader 308 before the loader 308 is placed in contact with the gel 102. Furthermore, because the loader 308 remains in contact with the gel 102 during the electrophoresis process, the structural integrity problems associated with the sample wells formed by the prior art sample loaders are eliminated. Moreover, undesirable sample material such as urea can be easily and quickly removed using the present sample loader. In contrast, as described above, the removal of undesirable sample material from the sample wells formed by the prior art sample loaders is a difficult and time-consuming process. Thus, the present sample loader 308 overcomes many of the drawbacks associated with the prior art sample loading devices and methods.

FIGS. 5a and 5b show the sample loader of FIGS. 3a and 3b intended for use in the horizontal EGS 200 described above with reference to FIGS. 2a and 2b. As shown in FIG. 5a, the gel 204 is cast between two removable dams 202 before the insertion of sample material into the gel 204. After the gel 204 polymerizes, the dams 202 are removed from the device 200.

The device 200 is then filled with electrode buffer solution 408 to a level 116 which just exceeds an upper surface 220 of the gel 204. After the device 200 is filled with the electrode buffer solution 408 to the level 116, sample material 316 is applied to the loading areas 312 and the membranes 306 of the sample loader 308 as described above with reference to FIGS. 3a and 3b. The sample loader 308 is then positioned within the EGS 200 so that the loading areas 312 of the fingers 310 are positioned proximate a top edge 314 of the gel 204. Thus, the sample material 316 contacts the gel 204 at the upper edge 314 as shown in FIG. 5b. As described above, the membranes 306 diffusion-isolate the sample material so that the sample material is reversibly bound to the membranes 306. Consequently, very little of the sample material diffuses into the gel 204 until the gel is activated by a release mechanism. An electric field is then applied to the gel 204 via the cathode wire 206 and anode wire 208 as described above with reference to FIG. 2b. The biomolecular samples are then substantially released by the loader 308 and loaded into the gel 204.

Figure 6A:
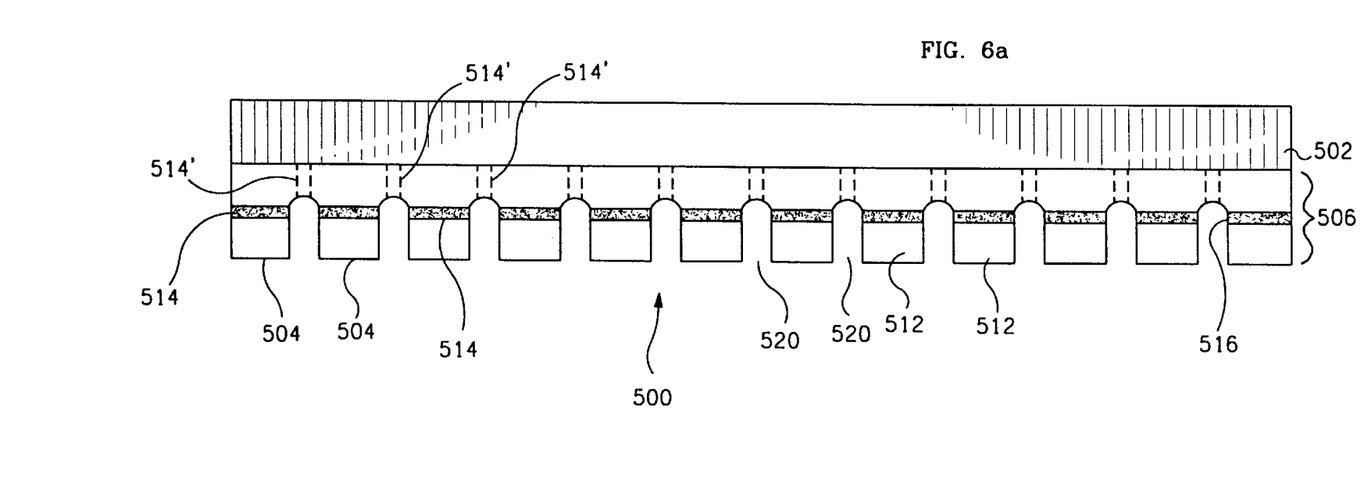
FIG. 6a is a front plan view of another preferred embodiment of the sample loader of the present invention.

FIG. 6a shows details of a preferred embodiment of the sample loader of the present invention. As shown in FIG. 6a, the sample loader 500 preferably comprises a substrate 502 and a plurality of fingers 504. A lower portion of the substrate 502 includes a membrane 506 which diffusion-isolates applied sample material by reversibly binding the sample material to the fingers 504 of the sample loader 500. The thickness of the membrane 506 may be varied to hold different sample amounts. Sample loading areas 512 can be further defined in the fingers 504 by a plurality of sample inhibiting agents 514 which are formed through the membrane 506. For example, the sample inhibiting agent 514 may comprise hydrophobic ink which extends through each membrane 506 to the substrate 502 across the proximal end of each finger 504, as shown. The hydrophobic ink 514 inhibits the migration or diffusion of sample material from one finger 504 to another. The position of the ink 514 on each finger may also be used to define and control the size of the sample loading area of the membranes 506.

Alternatively, the hydrophobic ink 514 can be positioned within the membrane 506 in any configuration which inhibits the inadvertent diffusion of sample material from one finger 504 to another. For example, as shown in FIG. 6a, the hydrophobic ink 514' is vertically formed through the membrane 506 so that the ink 514' is equidistant between the fingers 504.

As described above, the membrane 506 preferably comprises material which diffusion-isolates and reversibly binds the biomolecular sample material before activation of a release mechanism, such as the application of an electric field. The material binds and substantially retains ("releasably retains") the sample material to the loading area 512 when it is immersed in a standard electrophoretic buffer solution. However, when an electric field is applied to the buffer solution, the membrane 506 preferably releases a substantial portion of the bound sample material into the gel for separation and identification. After applying an electric field to the gel, the sample transfer rate from the loading areas 512 to the gel is preferably substantially equivalent to the transfer rates between the sample wells and the gels in the prior art apparatuses. The resolution of the sample bands produced using the present loader 500 and the resolution of the sample bands produced using the prior art apparatuses are also preferably substantially equivalent.

By definition, a membrane on which sample material will be "releasably retained" cannot be one on which sample is retained by absorption. If sample is merely absorbed by the membrane, the sample will diffuse from the membrane on contact with the gel. Similarly, membranes to be used in the device of the invention should not bind the sample so tightly that release of the sample into the gel is prevented. Rather, membranes suitable for use in the invention are those on which sample is retained even after contact with the gel and until a releasing mechanism (i.e., an electric field or pH change) is applied to the membrane.

To this end, membranes suitable for use in the device of the invention will be those which covalently bind the preferred sample materials to be tested. As such, membrane 506 has no net positive charge; i.e., membrane 506 has either a net neutral charge, net negative charge or no charge, with net negatively charged or uncharged membranes being preferred for their lack of positively charged regions. Preferred membrane materials are therefore negatively charged or uncharged nitrocelluloses and, less preferably, neutrally charged nylons (which have a slight positive charge). Examples of suitably charged nitrocellulose materials include BA85 (a product of Schleicher & Schuell), Biotrace® (a product of Gelman) and Bioblot NC® (a product of Costar). Examples of suitable neutrally charged nylons include Biotrans® (a product of ICN) and Immobilon-S® (a product of Millipore). For ease of reference in this regard, a comparison of several commercially available nitrocellulose and nylon membranes for their performance in the device of the invention is provided in Example II below.

The selection of particular membrane material selected for use with the present sample loader is made according to the type of samples which are to be applied to the membrane. For example, DNA molecules appear to be more easily bound and retained by the membranes investigated than are RNA molecules. Similarly, using both native and denaturing conditions, proteins are less effectively bound and retained by the membranes than are DNA molecules. However, the RNA samples generally are released into the gel solution upon activation just as effectively as are the DNA samples. Thus, among the samples preferably loaded by the present sample loader 500 are double-stranded DNA (dsDNA), single-stranded DNA (ssDNA), RNA, and proteins.

Also, the membrane's performance can vary under varying conditions of buffer solution pH, temperature, salt concentration, and strength. These varying conditions can affect the amount of electric charge required to fully release the samples from the membrane 506. Moreover, pre-wetting, pre-spotting, and drying time for pre-treated membranes, varying sample volume and the magnitude of the electric field applied to the buffer solution, can also affect membrane performance. Those of ordinary skill in the art will be familiar with the suitable parameters for these typical laboratory conditions for electrophoresis. Thus, the membrane 506 shown in FIG. 6a preferably is used to load any type of biomolecular sample material into an electrophoretic gel under typical laboratory conditions.

Although some specific sample and membrane materials have been described, they should not be taken as limiting the scope of the present invention. The present invention contemplates the use of any membrane having a net neutral charge, net negative charge or no charge for releasably retaining sample material (i.e., which releases a substantial portion of the sample material into the gel after the system is activated by a release mechanism).

Referring again to FIG. 6a, the present sample loader 500 preferably includes a substrate 502 which structurally supports the membrane 506. The substrate 502 preferably comprises a non-conductive, relatively inert, non-porous, neutrally charged, inexpensive material. The substrate preferably comprises either celluloid or plastic. The substrate 502 may be manufactured using a number of techniques. For example, the substrate 502 may first be cut to a desired width. The fingers 504 may then be formed in one side of the substrate 502 by cutting, scoring or punching away areas 520 between the fingers 504. Preferably, the fingers 504 are formed sufficiently long to prevent capillary action or wicking of buffer solution from contaminating the samples applied to the membrane loading areas. Similarly, the fingers 504 are preferably sufficiently long to prevent wicking of a sample from a first loading area 512 to a second loading area 512 on another finger 504.

Preferably, the present sample loader 500 is manufactured by placing the substrate 502 (which is typically formed into strips) into a membrane slurry material. The membrane slurry is placed n contact with the substrate 502 until it solidifies upon the surface of the substrate. The fingers 504 are formed in the substrate by punching or cutting away areas between the fingers. Sample loading areas 512 are defined in the fingers 504 by scoring substantially horizontal lines across approximate midpoints of the fingers 504. During the scoring process, the solidified membrane material is cut away from the substrate 502. The substrate 502 is left in tact. In one preferred embodiment, the scored membrane is filled with hydrophobic ink 514 as shown in FIG. 6a and described above. Other alternative embodiments use photoetching or photomasking techniques to define the sample loading areas 512.

The membrane 506 may be formed on the finger side of the substrate 502 by any convenient method, such as screening liquid membrane material to the substrate 502 or dipping the substrate 502 into a liquid membrane pool for a time which is sufficient to allow the membrane material to adhere to the substrate 502. Alternatively, the membrane may be formed by cutting membrane bulk material into strips of equal widths and affixing the strips on the substrate 502 as shown in FIG. 6a. That is, the strips of membrane can be used to define the fingers 504 of the sample loader 500. In one preferred embodiment, the membrane comprises sheets of plastic-backed nitrocellulose material available from Schleicher & Schuell.

Figure 6B:
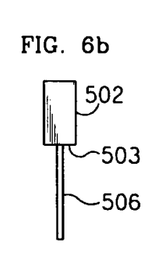
FIG. 6b is a side view of an alternative embodiment of the sample loader of the present invention.

As described above with reference to FIG. 3a, one alternative embodiment of the sample loader 500 shown in FIG. 6a eliminates the necessity for the substrate 502. If the membrane 506 comprises material which is sufficiently rigid, and if the membrane 506 is sufficiently thick, the entire substrate 502 can be replaced with membrane material (i.e., the membrane 506 is used as the substrate). The fingers 504, sample loading areas 512, and sample inhibiting agents 514 (if necessary) are formed into the membrane as described above with reference to the preferred embodiment. Also, in another alternative embodiment shown in side view in FIG. 6b, the substrate 502 is substantially thicker than the substrate of the preferred embodiment and the membrane 506. In this alternative embodiment, the relatively thin membrane 506 and fingers 504 are attached as "legs" to the bottom 503 of the substrate 502.

Figure 6C:
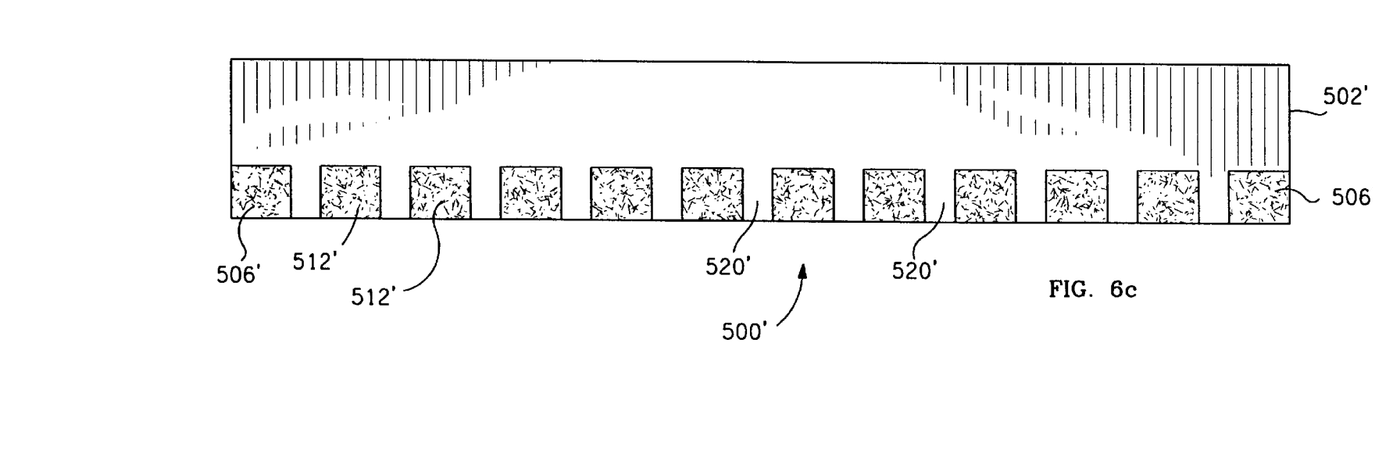
FIG. 6c is a front plan view of another preferred embodiment of the sample loader of the present invention.

FIG. 6c shows a front plan view of yet another alternative embodiment of the present invention. The embodiment of FIG. 6c is similar to that shown in FIG. 6a with the exception that the fingers 504 have been replaced by "virtual fingers" which are formed into the substrate 502'. The sample loader 500' shown in FIG. 6c is preferably manufactured by screening membrane material 506' onto a sample loading portion of the substrate 502' and thereby creating sample loading areas 512' (or "virtual fingers") onto the substrate 502'. As described above with reference to FIG. 6a, the sample loading areas 512' diffusion-isolate sample material which is applied thereto until the membrane 506' is activated by a release mechanism. The notches 520 of FIG. 6a are replaced by the virtual notches 520' which are merely areas of diffusion-isolation between the sample loading areas 512'. The embodiment shown in FIG. 6c is useful in EGS applications which do not require sample loading fingers which extend downwardly toward the EGS gel.

The alternative embodiment shown in FIG. 6c can alternatively be manufactured by first applying or affixing membrane material to the sample loading portion of the substrate 502', and then scoring the membrane 506' to create the virtual notches 520' (i.e., areas where membrane material is removed from the substrate 502') as shown in FIG. 6c. Alternatively, the sample loading areas 512' can be diffusion-isolated from each other using a chemical isolation means such as the hydrophobic ink described above with reference to FIG. 6a. If hydrophobic ink is used, the loading areas 512' can be formed by first deeply scoring into the membrane 502' and thereafter filling the scored portions of the substrate with the ink.

Figure 7:
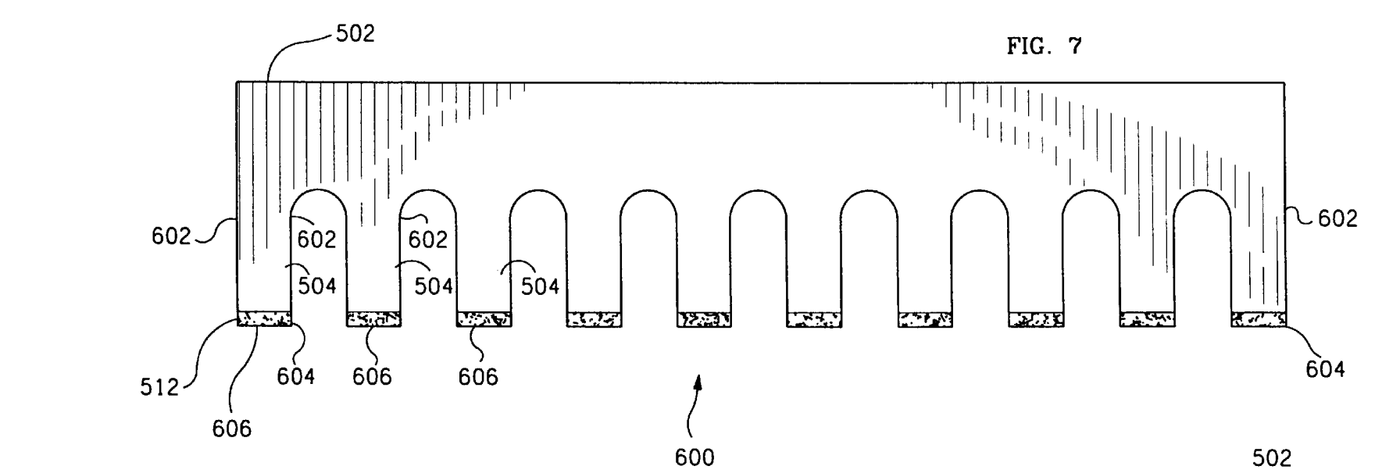
FIG. 7 is a front plan view of an end-loaded sample loader in accordance with the present invention.
Figure 8:
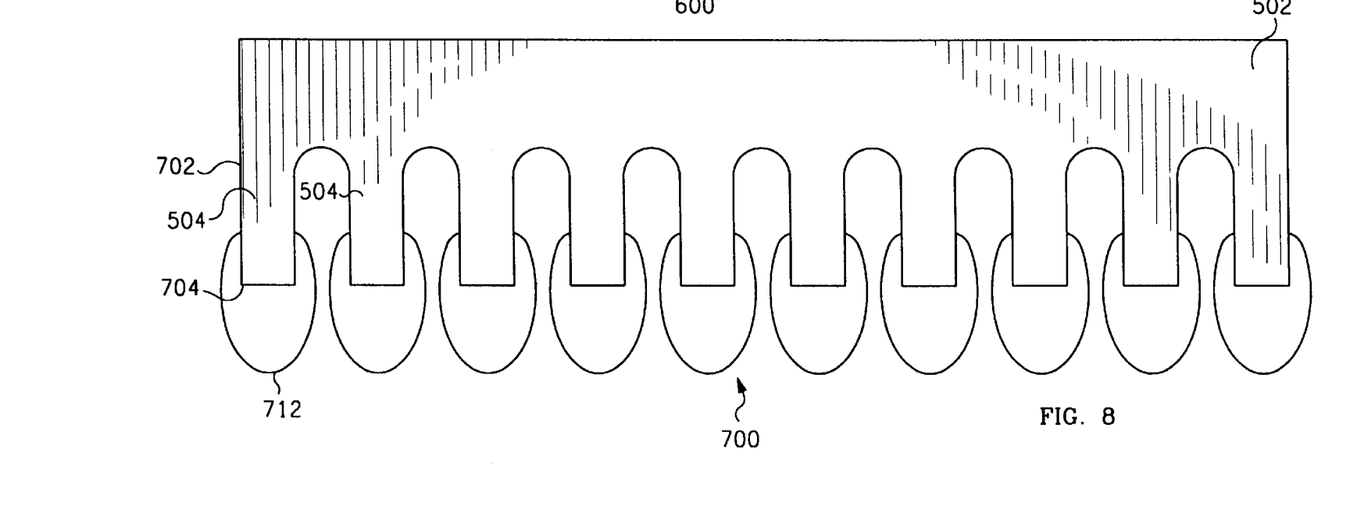
FIG. 8 is a front plan view of an alternative embodiment of the end-loaded sample loader of FIG. 7.

Other alternative embodiments of the present sample loader are shown in FIGS. 7 and 8. FIG. 7 shows an end-loaded sample loader 600. Similar to the sample loader of FIG. 6a, the end-loaded sample loader 600 preferably includes a substrate 502, a plurality of teeth or sample loading fingers 504, each having a proximal end 602 and a distal end 604, wherein the fingers extend downwardly away from the proximal end 602, a sample loading area 512 at the distal end 604 of the fingers 504, and a membrane 606. The membrane 606 is affixed to the distal end 604 of the fingers 504 so that only a very small percentage of the total finger length is covered by the membrane 606. In contrast, as described above, the membrane 506 of the sample loader 500 of FIGS. 6a and 6b covers a substantial length of the fingers. Using the end-loaded sample loader 600 of FIG. 7, sample material is applied to the sample loading areas 512 by simply dipping or otherwise adhering the sample material to the membranes 606. For conventional EGS, the membrane 606 should be sufficient to hold a sample in solution where the drop volume is at least approximately 0.3 $\mu$L.

If the fingers 504 are sufficiently long, the loader does not require use of a sample inhibiting agent such as the hydrophobic ink described above with reference to the preferred embodiment shown in FIG. 6. Because a sample is applied only to the distal end 604 of a finger 504, and not along the entire length of the finger, the sample is less likely to diffuse from one finger to either the buffer solution or another finger. Therefore, the longer the fingers 504, the less potential for sample or buffer contamination and cross-talk. However, an alternative end-loaded sample loader might include such a sample inhibiting agent similar to that described above with reference to FIG. 6. As described above, if included, the sample inhibiting agent preferably comprises hydrophobic ink which inhibits the migration or diffusion of sample material from one finger 604 to another. The ink is preferably positioned across the width of each finger 504 at the proximal ends 602 of the fingers 504. As described above with reference to the preferred embodiment, the membrane 606 can alternatively serve as its own substrate.

FIG. 8 shows another alternative embodiment of the end-loaded sample loader of FIG. 7. Similar to the loader of FIG. 7, the sample loader shown in FIG. 8 preferably includes a substrate 502, and a plurality of sample loading fingers 504, each having a proximal end 702 and a distal end 704, wherein the fingers 504 extend downwardly away from the proximal end 702. The fingers 504 include a three-dimensional sample loading area 712 which surrounds the distal end 704 of the fingers 504. The sample loading areas 712 are preferably formed by dipping the fingers 504 into a pool of membrane material, removing the loader 700 from the pool of membrane material, and allowing the membranes to solidify into the colloidons shown in FIG. 8. Because the loading areas 712 are much more three-dimensional than the rectangularly-shaped loading areas 512 of the sample loader shown in FIG. 7 (the loading areas 512 are substantially two-dimensional), the loading areas 712 accommodate a greater volume of sample material than do the loading areas 512.

Before insertion of the sample loader fingers 504 into a gel of an EGS, samples are typically applied to the membranes covering the sample loading areas 712 and allowed to dry. Similar to the sample loader of FIG. 7, if the fingers 504 are sufficiently long, a sample inhibiting agent need not be used. Because samples are applied only to the sample loading areas 712, the samples are less likely to diffuse from one finger to another and thereby cause cross-contamination of samples. However, as with the loader of FIG. 7, an alternative end-loaded sample loader might include sample inhibiting agents similar to those described above with reference to FIGS. 6a and 6b. All of the embodiments of the present invention of an apparatus and method of loading samples into a gel of an EGS may also be used with the prior art systems which first form sample wells in the gels and then load the wells with the samples to be tested. The present invention may be used to load sample material into the sample wells after the gel polymerizes. Alternatively, the present invention may be used to load samples into sample wells previously formed by a prior art well-forming device.

Thus, in essence, the present invention is a sample loader for an EGS having well-defined diffusion-isolated sample loading areas. The sample loading areas preferably include a membrane which releasably retains applied sample material until and unless the membrane is activated by a release mechanism When immersed in a buffer solution and/or gel of an EGS, the sample material sufficiently adheres to the membrane so that the sample material does not diffuse substantially into the gel before activation of a release mechanism. However, when activated by a release mechanism, the membrane releases a substantial portion of the sample material into the gel and allows the sample material to undergo an electrophoretic process. A number of different means may be used to diffusion-isolate the loading areas. For example, the loading areas may be chemically-isolated using a hydrophobic ink. Alternatively, the substrate of the loader may be scored thereby forming "virtual fingers" in the substrate. Hydrophobic ink may alternatively be used to fill in the scored areas and thus further diffusion-isolate the virtual fingers.

A number of embodiments of the present invention have been described. Nevertheless, it will be understood that various modifications may be made without departing from the spirit and scope of the invention. For example, as described above, all of the embodiments of the present invention may use membrane material as the substrate of the loaders. Further, the shape of the various loaders described above and shown in the figures is exemplary only, and is not intended to restrict the scope of the invention. For example, although the fingers 504 (FIGS. 6–8) are rectangular in the embodiments shown and described, they could also be substantially pyramidical, spherical, cylindrical, parallelogram-like or triangular. Similarly, the fingers 504 can be longer or shorter depending upon the application. The shape of the substrate can also be alternatively modified. For example, the side of the sample holder which is grasped by a technician may be circularly-shaped, or may include a handle for easy handling. The width of the fingers and membranes can also be varied depending upon the amount of sample material to be loaded. Also, the loader can be manufactured by arranging parallel sheets of substrate under a single membrane sheet, and adhering the membrane to both sides of the substrates. Each parallel sheet thereby forms a finger of the sample loader. Furthermore, although the method of using the present sample loader discloses placing the sample loading areas into contact with the electrophoretic gel material, the present sample loader can also be used by inserting the sample loading areas and fingers into the gel.

Accordingly, it will be understood that the invention is not to be limited to the specific embodiments described above or to the embodiments illustrated by the following examples, but is defined only by the appended claims.

EXAMPLE I

STANDARD PROTOCOL FOR GEL ELECTROPHORESIS USING THE DEVICE OF THE INVENTION

1. Loading

Gel: The gel is placed onto a preheated heat sink maintained at 35° C., with an aluminum block on top. The gel temperature is equilibrated for 5–10 min.

Sample: Fresh $^{35}$S labeled Sequenase sequencing reactions should be prepared the same day prior to a gel run. The procedure utilized in testing this membrane included stopping the reactions with a mixture of 75% Sequenase stop solution and 25% glycerol, prepared fresh daily. The samples are denatured at 70° C. for 2 minutes after preparation.

Membrane loader: Membrane loaders (BA85; Schleicher & Schuell) are cut from sheets using a steel ruled die mounted on a press. The current configuration is an 8 tooth loader with dimensions 3 cm wide×2.5 cm long, and with tooth dimensions 5 mm long by 2.5 mm wide and with a 1 mm space between teeth. After pressing out 8 tooth loader cut in half to make two 4 tooth loaders.

Linear polymer: Prior to application of the sample to the membrane, 1 ml of 4% polyacrylamide prepared in water, and catalyzed with the same amount of APS and TEMED as above, is added to the well formed by the plug at one end. An equal amount is applied to the other end of the gel to form a seal with the buffer block that will be placed there.

Buffer blocks: Two are used for each gel. One is applied to the end opposite the loading well by pushing it into place perpendicular to the length of the gel prior to the run. The other is used for the same purpose at the loading end of the gel after the membrane loader is in place.

Application of sample: After the gel temperature is equilibrated and linear polyacrylamide solution is placed in the well, 0.75 ul of a fresh sequencing reaction are applied to the end of the desired membrane loader tooth with a pipetman. The sample will migrate up the tooth by capillary action. Five to ten seconds after application of the sample (until it appears that all of the sample is absorbed) the loader is placed into the well containing linear polyacrylamide. The second buffer block is placed over the back end of the loader and flush against the end of the top plate without disturbing loader positioning.

2. Electrophoresis

After the loader and buffer blocks are in place, the graphite electrodes are placed on top of the appropriate buffer blocks so the opposite ends are plugged into the power supply. The power supply is activated at 3000 volts constant, 35° C. (heat sink) for 20 minutes. This produces a banding pattern ⅔ to the full length of the gel.

EXAMPLE II

IDENTIFICATION OF MEMBRANES FOR RELEASABLY RETAINING SAMPLE MATERIAL

For ease of reference in selecting membranes for use as the membrane loader in the device of the invention, the performance of several commercially available membranes in the device was evaluated using the protocol set forth in Example I. Results were evaluated by observing sample retention by each membrane on insertion of the membrane into the gel and by measuring sample release from the membrane into the gel before and after application of a releasing mechanism (the electric field described in Example I). Band resolution on autoradiograms ("load quality") was compared after each gel run. For comparison, membranes having a positive charge (i.e., which lack the ability to releasably retain sample material on insertion into a gel) were also tested.

To maximize reproducibility, each membrane was tested 4 times on separate gels using 4 lane loaders. A standard membrane (Biotrace®, a negatively charged nitrocellulose product of Gelman) was tested on a fifth gel for comparison to each membrane tested. The results of these tests are set forth in Table I below. The results are expressed quantitatively in the rightmost two columns on a scale from 0 to 10, where 10 indicates performance comparable to standard and 0 indicates a performance unlike the standard (i.e., no sample retention and/or poor band resolution).

| No. | Manufacturer/Source | Membrane Name | Pore Size | Classification | Comments | Sample Release | Load Quality |
|---|---|---|---|---|---|---|---|
| 1 | Advantec | MTS | 0.45 um | Nitrocellulose | net negative | 10 | 9 |
| 2 | Amersham | Hybond N | | Nylon | net neutral charge | 9 | 6 |
| 3 | Bio-Rad | PVDF | 0.2 um | PVDF | no charge | 1 | 1 |
| 4 | Costar | Bioblot | 0.45 um | Nitrocellulose | net neutral charge | 10 | 10 |
| 5 | Denville | Hyblot Plus | | Nylon | positive charge | 0 | 0 |
| 6 | Gelman | Nitroflow V | 5 um | Nitrocellulose, 80–150 um thick | no charge | 10 | 10 |
| 7 | Gelman | Biotrace NT | 0.45 um | Nitrocellulose | no charge | 10 | 10 |
| 8 | Gelman | Supor 200 | 0.2 um | Hydrophilic Polyethersulfone | no charge | 10 | 10 |
| 9 | Gelman | Supor 100 | 0.1 um | Hodrophilic Polyethersulfone | no charge | 10 | 10 |
| 10 | Gelman | Supor 5000 | 5.0 um | Hydrophilic Polyethersulfone | no charge | 11 | 9 |
| 11 | Gelman | Ultrabind US-450 | 0.45 um | modified polyethersulfone, permanent c | no charge | 10 | 9 |
| 12 | Gelman | Versapor 450 | 0.45 um | Hydrophilic acrylic on support | no charge | 10 | 8 |
| 13 | Gelman | biotrace HP 400 | 0.45 um | polyethersulfone | positive charge | 0 | 0 |
| 14 | Gelman | Biotrace HP 200 | 0.2 um | polyethersulfone | positive charge | 0 | 0 |
| 15 | Gelman | Z-bind | 0.45 um | Post treated, modified polyethersulfone | no charge | 10 | 10 |
| 16 | Gelman | TR450 | 0.45 um | polysulfone on polyester | no charge | 10 | 10 |
| 17 | Gelman | I.C.E. P/n 66530 | 0.45 um | charged polyethersulfone, neg. Sulfoni | negative charge | 11 | 9 |
| 18 | ICN | Biotrans | 0.2 um | Nylon, 50% amino 50% carboxyl | net neutral charge | 9 | 6 |
| 19 | Inotech | IH-400 | 0.45 um | Nylon | no charge | 2 | 1 |
| 20 | Inotech | IH-400 | 0.45 um | Nitrocellulose | net neutral charge | 10 | 10 |
| 21 | Lida | Nitrocellulose | 0.45 um | Nitrocellulose | no charge | 10 | 10 |
| 22 | Millipore | Immobilon NC | 0.45 um | Nitrocellulose | no charge | 10 | 10 |
| 23 | Millipore | Immobilon P | 0.45 um | PVDF | no charge | 1 | 0 |
| 24 | Millipore | Immobilon S | 0.45 um | Neutral nylon | no charge | 2 | 2 |
| 25 | MSI | Nitropure | 0.45 um | Supported nitrocellulose | net neutral charge | 10 | 10 |
| 26 | MSI | Nibrobind | 0.45 um | Nitrocellulose | net neutral charge | 10 | 10 |
| 27 | MSI | PVDF Plus | 0.45 um | PVDF | no charge | 1 | 1 |
| 28 | MSI | Nitroplus NC | 0.45 um | Nitrocellulose | net neutral charge | 10 | 10 |
| 29 | MSI | Magnagraph | 0.45 um | Chemically optimized nylon | net neutral charge | 3 | 2 |
| 30 | Sartorius | Nitrocellulose | 0.45 um | Nitrocellulose | net neutral charge | 10 | 10 |
| 31 | Sartorius | Supported Nitrocellulose | 0.2 um | Supported Nitrocellulose | net neutral charge | 10 | 10 |
| 32 | Schleicher & Schuell | Nytran | | Nylon, polyimide grps + charge | net neutral/positive charge | 1 | 0 |

-continued

| No. | Manufacturer/Source | Membrane Name | Pore Size | Classification | Comments | Sample Release | Load Quality |
|---|---|---|---|---|---|---|---|
| 33 | Schleicher & Schuell | BA 75 | 0.05 um | Nitrocellulose | negative charge | 10 | 9 |
| 34 | Schleicher & Schuell | AE 98 | 5.0 um | Nitrocellulose | negative charge | 10 | 10 |
| 35 | Schleicher & Schuell | AE 100 | 12.0 um | Nitrocellulose | negative charge | 10 | 10 |
| 36 | Schleicher & Schuell | NA 45 | 0.45 um | DEAE cellulose | positive charge | 0 | 0 |
| 37 | Schleicher & Schuell | Nytran plus | 0.45 um | nylon | positive charge | 0 | 0 |
| 38 | Schleicher & Schuell | BA 85 | 0.45 um | Nitrocellulose | negative charge | 10 | 10 |
| 39 | Vanguard | Nitrocellulose | 0.45 um | Nitrocellulose |  | 10 | 10 |
| 40 | Whatman | Nitrocellulose | 0.45 um | Nitrocellulose | net negative | 10 | 10 |

We claim:

1. A method of loading samples into a gel of an electrophoretic gel system, comprising the steps of:

(a) applying a sample to a membrane, wherein the membrane accepts and retains the sample thereon even when placed in contact with the gel until means for actively releasing the sample from the membrane are applied thereto;

(b) contacting the sample loaded membrane with the gel; and (c) applying the means for releasing the sample to the gel so the sample is released from the membrane into the gel.

2. The sample loading method of claim 1, wherein the membrane used to apply sample in step (a) reversibly binds each applied sample via an ionic affinity between molecules of the membrane and each applied sample.

3. The sample loading method of claim 1, wherein the means for releasing sample from the membrane comprises applying an electric field to an electrode buffer solution.

4. The sample loading method of claim 1 wherein the membrane used to apply sample in step (a) is composed of nitrocellulose.

5. The sample loading method of claim 1 wherein the membrane used to apply sample in step (a) is composed of nylon.

6. The sample loading method of claim 1 wherein the membrane used to apply sample in step (a) is composed of polysulfone.

7. The sample loading method of claim 1, wherein the membrane used to apply sample in step (a) has a net negative charge, net neutral charge or no charge.

8. An electrophoretic gel system comprising:

an electrophoretic gel;

a membrane having a sample applied to and retained thereon, the membrane and sample being in contact with the gel; and means for actively releasing the sample from the membrane into the gel.

* * * * *